(12) United States Patent
Seidel et al.

(10) Patent No.: US 6,210,901 B1
(45) Date of Patent: Apr. 3, 2001

(54) SPECIFIC BINDING SUBSTANCES FOR ANTIBODIES AND THEIR USE FOR IMMUNOASSAYS OR VACCINES

(75) Inventors: Christoph Seidel; Rupert Herrmann, both of Weilheim; Eva Hoess, Starnberg; Hans-Georg Batz, Tutzing, all of (DE)

(73) Assignee: Roche Diagnostics GmbH, Manheim (DE)

( * ) Notice: Subject to any disclaimer, the term of this patent is extended or adjusted under 35 U.S.C. 154(b) by 0 days.

(21) Appl. No.: 08/682,791

(22) PCT Filed: Jan. 31, 1995

(86) PCT No.: PCT/EP95/00333

§ 371 Date: Jul. 31, 1996

§ 102(e) Date: Jul. 31, 1996

(87) PCT Pub. No.: WO95/20764

PCT Pub. Date: Aug. 3, 1995

(30) Foreign Application Priority Data

Jan. 31, 1994 (DE) ................................. 44 02 756

(51) Int. Cl.$^7$ ......................... G01N 33/541; C07K 38/10; A61K 39/29
(52) U.S. Cl. ..................... 435/7.1; 424/189.1; 424/225.1; 424/186.1; 424/185.1; 424/184.1; 530/326; 514/13; 435/7.9
(58) Field of Search .................. 435/7.1, 7.9; 424/189.1, 424/225.1, 186.1, 185.1, 184.1; 530/326; 514/13

(56) References Cited

U.S. PATENT DOCUMENTS

| | | | |
|---|---|---|---|
| 5,565,548 | * 10/1996 | Neurath et al. | 530/324 |
| 5,639,854 | * 6/1997 | Sia et al. | 530/324 |
| 5,773,572 | * 6/1998 | Fishleigh et al. | 530/324 |
| 5,843,639 | * 12/1998 | Peyes et al. | 435/5 |

* cited by examiner

*Primary Examiner*—T. D. Wessendorf
(74) *Attorney, Agent, or Firm*—Fulbright & Jaworski, LLP

(57) ABSTRACT

The invention relates to derivatives of hepatitis C virus amino acid sequences. These derivatives can be used to screen samples, such as blood, to determine if antibodies to hepatitis C virus are present.

14 Claims, 8 Drawing Sheets

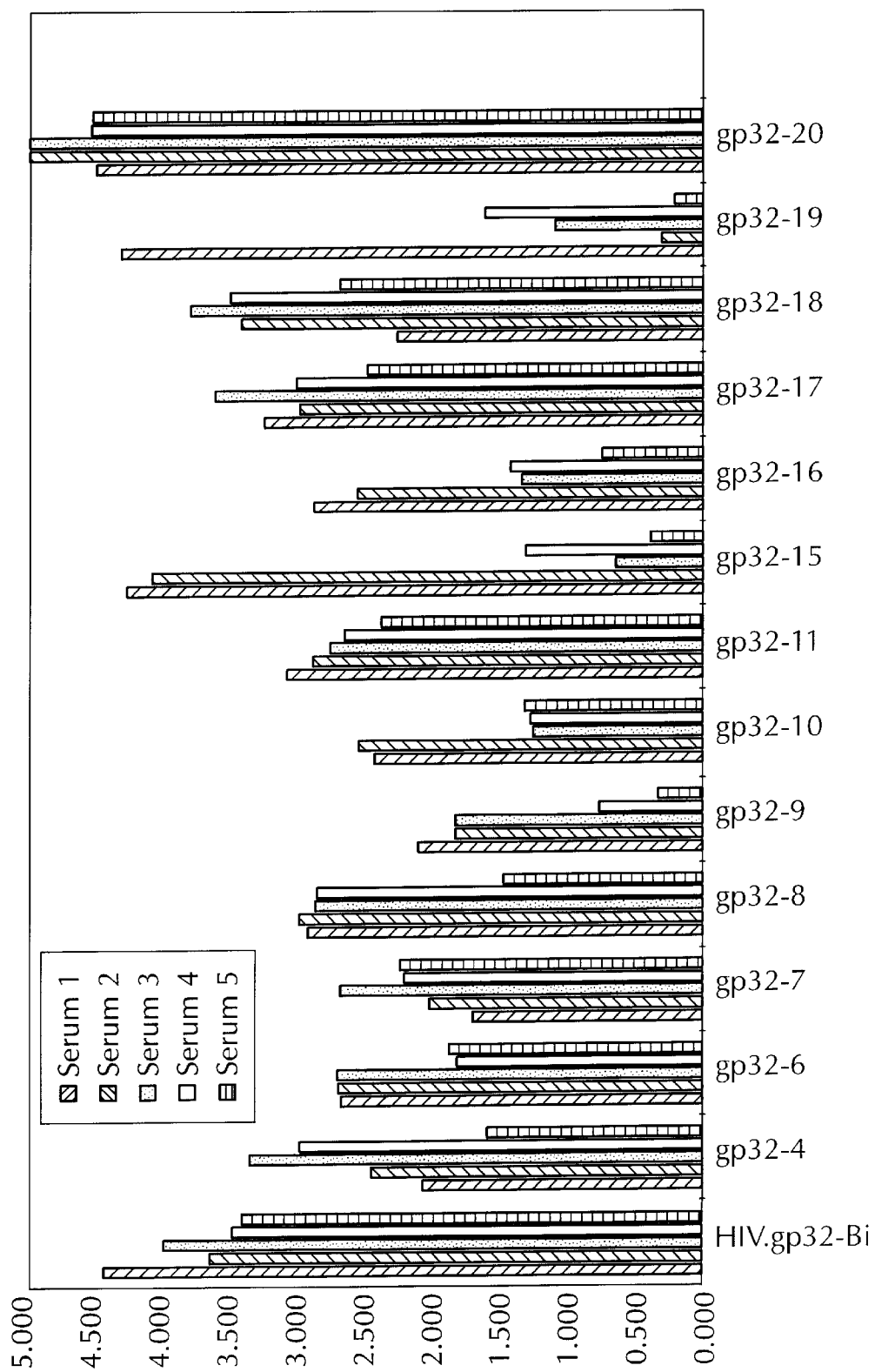

SPECIFIC BINDING SUBSTANCES FOR ANTIBODIES AND THEIR USE FOR IMMUNOASSAYS OR VACCINES

FIELD OF THE INVENTION

The invention concerns specific binding substances for antibodies, their use in immunoassays and as vaccines as well as an immunological method of determination using this specific binding substance as a binding partner for the antibody.

BACKGROUND AND PRIOR ART

Antibodies are known to bind their corresponding antigens extremely specifically. If an antibody is directed against a partial amino acid sequence of a protein (an epitope), it is known that this partial sequence can be used alone for its binding.

The specific binding of two biomolecules was compared to the lock and key principle for the first time in the case of enzyme-substrate binding. However, in the 60s Linus Pauling recognized that there was a fundamental difference between enzyme-substrate binding and antibody-antigen binding. The binding site of an enzyme does not completely fit the substrate at all. Rather the binding site of an enzyme appears to be much more similar to the structure of the transition state of a substrate reaction and therefore allows the substrate to have a certain latitude in its structure without the enzyme losing its binding properties for the substrate. In contrast absolute fitting of the antigenic epitope into the binding site of the antibody is required for antigen-antibody binding, which basically excludes any spatial variation of the epitope with regard to antibody binding. It is only by means of this specific epitope/antibody binding that a foreign substance can be specifically eliminated from the organism by an antibody.

Epitopes toward which an antibody is specifically directed are mainly used for two applications. On the one hand, they serve—usually bound to a carrier—as immunogens (vaccines) which cause an organism to produce antibodies which are directed against these epitopes or against antigens which contain these epitopes. On the other hand, such epitopes are used in immunoassays for the specific detection of antibodies in body fluids in which they have been produced by an immune reaction to antigens which contain these epitopes (for example after infection by an infectious organism).

If the epitopes are polypeptides, when they are used in the organism as a vaccine or when they come into contact with body fluids such as serum in diagnostic applications, there is a problem in that the polypeptides are decomposed and lose their function by metabolic degradation, brought about in particular by proteases such as those which occur in body fluids.

It is known that polypeptides which are used for therapeutic purposes, i.e. for binding to enzymes or to hormone receptors in the organism, can be protected from metabolic degradation in the body by modifying the amino acid sequence. A description of such so-called peptide mimetics as therapeutic agents and the production thereof is given inter alia in Giannis, "Angewandte Chemie" 105 (1993) 1303–1326; Lee, Bull Chem. Soc. Jpn 66 (1993) 2006–2010 and Dorsch et al, "Kontakte" (Darmstadt) 1993 (2). However, this modification method did not appear to be applicable to epitopes used for binding antibodies and as immunogens for producing antibodies due to the known high specificity of the epitope-antibody binding.

Recently, at the third European BIAcore Symposium in London 1993, peptide human serum albumin fusion products were proposed for stabilizing such polypeptide epitopes (Integration of Biocore in the Discovery Department S. Reboul et al). However, the coupling of peptide epitopes to human serum albumin merely delays the enzymatic degradation of the polypeptides to a certain extent but does not prevent it.

SUMMARY OF THE INVENTION

The object of the invention is to provide binding substances which function as epitopes for vaccines useful in producing antibodies and in immunoassays for the detection of antibodies which are directed against epitopes with particular natural amino acid sequence. These inventive substances have modified metabolic stability, in particular a modified protease stability, or modified duration of action as an immunogen in an animal organism or as a binding partner in immunoassays using body fluids as the sample material. These inventive substances can, nevertheless, specifically and selectively bind an antibody which is directed against a corresponding natural epitope or produce this antibody in an immune response.

The object is achieved by the invention as characterized herein. It was found, surprisingly that, despite the extremely high specificity of the antigen-antibody reaction, a structural change in a natural epitope polypeptide sequence made by modifying the amino acids in the sequence in the manner according to the invention does not prevent binding of the modified epitope to an antibody which is directed against the unmodified epitope. However, compared to the unmodified epitope, the modified epitope has different metabolic properties when contacted with body fluids or in an animal organ e.g. a modified stability towards endogenous proteases.

DETAILED DESCRIPTION OF PREFERRED EMBODIMENTS

According to the invention the following possibilities are understood as a modification of the amino acids of the amino acid sequence of the natural epitope:

a) Substitution of the —CO—NH group of at least one peptide bond, by a diatomic or triatomic bridge (backbone modification).

A diatomic bridge is preferably understood as an —NH—CO—, $—CH_2—CH_2—$, —CH═CH, $—CH_2—NH—$, $—NH—CH_2—$, $—O—CH_2—$, $—CH_2—O—$, $—CH_2—S$ or $—S—CH_2—$ group. A triatomic bridge is preferably understood as a $—CH_2—CH_2—CH_2$ group in which a $—CH_2$ group can also be replaced by an —O— or —NH—, —S— or —CO— group. Diatomic bridges are preferred.

A $—CH_2—CH_2—$, $—CH_2—NH—$ or —NH—CO group is especially preferred. If a peptide —CO—NH group is for example replaced by a —NH—CO group, one formally obtains a diamine and a dicarboxylic acid from two amino acids of the natural epitope. If a —CO—NH group is for example replaced by a $—CH_2—CH_2—$ group, one obtains an aminovaleric acid derivative within the sequence of the binding substance according to the invention.

b) Extension or shortening of the side chains of at least one amino acid of the natural epitope. In this case it is preferable to incorporate an additional $—CH_2—$, —S—, —O—, —NH—, $—SO_2—$, —CO— group or to omit β-methylene groups in the side chain. It is especially preferred to carry this out in the side chains that are present in all amino acids of the epitope. If only one side chain is modified, a natural amino acid should not be formed in this process.

c) Substitution of a natural amino acid of the natural epitope by one or several non-biogenic L- or D-amino acids of the formula

wherein

R' represents hydrogen and

Y represents a (CH$_2$)n group in which n=2-8 or a —CH—(CH$_2$)m-CR$^1$R$^2$R$^3$ group in which m=0–3 in which R$^1$, R$^2$ and R$^3$ can be the same or different, and may represent hydrogen, a branched or unbranched C$_1$–C$_4$ alkyl residue or a phenyl, napthyl or 5-6-membered heteroaryl residue containing an O, S or N which can be substituted with methyl, halogen, NH$_2$, OH or carboxy or in which Y represents a CHR group in which R represents a side chain of a natural amino acid in which a —CH$_2$— group is replaced by —S—, —NH—, —CH=, —SO$_2$—, —CO— or —O— or in which at least one H atoms on said residue are substituted by CH$_3$, NH$_2$, carboxyl, SH, halogen or hydroxy, wherein in all cases Y is a group which does not occur in any natural amino acid or wherein R' is methyl, ethyl or phenyl and Y represents a CHR group in which R is a side chain of a natural amino acid.

In this case halogen is understood as F, Cl, Br or iodine, in particular Cl. Among heteroaryl residues pyridine, pyrrol, furan and thiophene are particularly preferred.

The binding substance according to the invention binds those antibodies which are directed against an antigen with a corresponding epitope consisting of a natural amino acid sequence. In particular these include antibodies which are directed against an epitope of an infectious organism. Examples are the epitopes of HCV or HIV.

An epitope with a natural amino acid sequence is understood as the minimum amino acid sequence composed of natural amino acids of a natural antigen, for example an infectious organism, which is necessary to bind an antibody produced by the antigen. These are amino acid sequences composed of at least six amino acids preferably at least 10 amino acids. Of course further amino acids can be joined to the epitope amino acid sequence at the C- or N-terminal end. However, these no longer make an important contribution to the binding of the antibody. The immunological binding substance according to the invention should at least correspond to this amino acid sequence of the natural epitope, but with at least one site within this amino acid sequence being modified in the manner according to the invention.

A —CO—NH— group of a peptide bond is preferably substituted according to the invention, preferably at a position in the sequence at which the associated amide bond is particularly vulnerable to cleavage by a protease. In this connection it is not necessary to substitute a —CO—NH— group by an atom group that is stable to hydrolysis at each possible protease cleavage site. A person skilled in the art knows the concentrations and types of relevant proteases in various body fluids. Proteases which occur frequently include trypsin, chymotrypsin, collagenase, elastase, thrombin, plasmin and kallikrein (e.g. N. Katunuma et al., Japan, Sci. Soc. Press. Tokyo/Springer Verlag Berlin, page 37–44 (1983)). In addition he will also know the respective amino acid sequences of the cleavage sites of different proteases. In addition, there are also unspecific proteases. Protease cleavage sites at the ends of an amino acid sequence are particularly vulnerable to cleavage. In this case the amino acid sequence is particularly at risk due to degradation by exopeptidases. In addition, peptide sequences containing glycine are particularly vulnerable to cleavage since the absence of a side group in glycine especially favours a hydrolytic attack by an unspecific protease. The modification according to the invention of an amide bond vulnerable to peptidase attack, in particular of a glycine peptide bond alone, can already lead to a substantially improved stability of the binding substances according to the invention compared to the natural epitopes with regard to degradation by proteases.

The protease stability of a binding substance according to the invention can be determined by exposing it to e.g. pancreatin, a mixture of frequently occurring proteases (including carboxy-peptidase A and B, trypsin, pepsin, chymotrypsin, elastase) or pronase (including aminopeptidase, carboxypeptidase, alkaline and neutral proteinase). The reduced enzymatic degradation of the binding substance can be determined by HPLC analysis of the appearance of peptide fragments over time.

It is especially preferred to replace a —CO—NH— group by —$CH_2$—$CH_2$—, $CH_2$—NH— or an NH—CO group.

An additional blocking of the sequence termini additionally stabilizes the binding substance towards exopeptidases.

The immunological binding substance is either coupled to a detectable marker molecule, to a solid phase or to a specific binding molecule which can specifically bind to a solid phase. This is preferably a covalent coupling either directly via the C- or N-terminal end of the binding substance or binding via a spacer.

A detectable label can directly or indirectly generate a measurable signal, for example by means of radioactivity, chemiluminescence, phosphorescence, fluorescence or electrochemiluminescence or by a visible colour. An indirectly measurable signal is present, for example, when an enzyme label is used. In this case a colour is formed by addition of an enzyme substrate. Examples of enzyme labels are: β-galactosidase, alkaline phosphatase or peroxidase.

The binding substance is bound to a solid phase according to methods familiar to a person skilled in the art. Beads, plastic tubes, microtitre plates or test carriers may serve as solid phases.

The immunological binding substance can also be coupled to a specific binding molecule via which it can bind to a solid phase. A preferred example is biotin which is preferably bound to the N-terminal end of the binding substance and can specifically bind to a surface coated with streptavidin.

The binding substance according to the invention can be used advantageously in immunoassays. It can be used particularly advantageously in immunoassays which are based on the sandwich principle for the detection of an antibody which is directed against an epitope with a corresponding natural amino acid sequence by incubating the antibody containing sample with two binding partners which specifically bind to the antibody and determining the formation of the binding partner antibody-binding partner complex in a suitable manner characterized in that at least one of the binding partners is a binding substance according to the invention.

Such an immunoassay is preferably carried out as a heterogeneous immunoassay. In this method one of the binding partners is either bound directly or via a spacer to a solid phase or is bound to a specific binding site, for example biotin, which can bind to the solid phase during the immunoassay. A binding substance according to the invention is used as this binding partner.

The second binding partner is labelled. Either a binding substance according to the invention provided with a marker molecule or a labelled anti-antibody directed against the antibody to be detected can be used for this binding partner. Preferred labels are enzyme labels or direct labels e.g. metal sols.

In order to carry out the immunoassay a sample of the antibody to be detected is incubated simultaneously or successively with the first binding partner, the labelled binding partner and the solid phase to form a solid phase-bound complex composed of the first binding partner, antibody and labelled binding partner. Then non-bound labelled binding partner in the liquid phase is preferably separated from the bound labelled binding partners on the solid phase and the label is measured in one of the two phases as a measure of the presence or concentration of the antibody to be determined. For example in the case of enzyme labels the enzyme-substrate solution is added to this for the measurement. The measurement can be carried out e.g. visually or photometrically.

A further aspect of the invention is an immunogen or a vaccine containing a binding substance according to the invention which is coupled to an amino acid sequence which contains a T-cell epitope or to a carrier molecule.

The vaccine is used for the preventive treatment of infections which are caused by antigens which contain an epitope with the respective natural amino acid sequence. In order to be used as an immunogen the C- or N-terminal end of the binding substance according to the invention has to be bound either to a suitable high molecular weight carrier protein such as keyhole limpet hemocyanin, hemocyanin, bovine serum albumin or edestin. It can be coupled e.g., at the N-terminal end of the amino acid sequence via maleinimidohexanoic acid-N-hydroxy-succinimide ester. Since in general vaccines (immunogens) are also T or B cell epitopes which are peptides by nature, the binding substance according to the invention can also be coupled to an amino acid sequence which contains a T cell epitope.

The vaccine is present in a pharmacologically effective dose together with and a pharmaceutically acceptable formulation.

Although antibodies against an artificial epitope which has an amino acid structure different from the natural epitope are produced in an immune response, these antibodies also bind to the natural epitope and can thus be used for immune defense against antigens which contain this epitope. However, due to the modification of their sequence they have an altered behaviour with regard to their metabolism in the animal organism e.g. a modified protease stability.

The immunogens according to the invention can also be used to obtain antibodies by common immunization procedures. These antibodies can be used to detect antigens which contain the amino acid sequence of the natural epitope in an immunological method of determination.

A further object matter of the invention is therefore a process for the production of antibodies which are directed against an epitope with a natural amino acid sequence which is characterized in that a mammal is immunized with a corresponding binding substance according to the invention which is linked to a molecule which contains a T cell epitope, e.g. a carrier protein molecule, and the antibodies that are produced are isolated by known processes, for example, from the serum or the spleen.

The binding substances according to the invention have, on the one hand modified metabolic behaviour in the organism in particular modified protease stability. Despite their modification they selectively bind in an immunoassay against antibodies which are directed against the natural epitope. Surprisingly it was additionally found that the binding substances according to the invention, particularly those with a substitution of a CONH group (backbone modification), can sometimes detect serum conversion at an earlier stage when monitoring freshly infected patients. In addition a specific detection of zero sera is possible with the binding substances according to the invention in particular using those with a side chain modification, while the sensitivity for positive sera is comparable with the natural epitopes.

It is possible to produce the binding substance according to the invention according to methods of peptide synthesis familiar to a person skilled in the art (e.g. Merrifield, JACS 85 (1964), 2146). A further object of the invention is therefore a process for the production of the binding substances according to the invention which consists of binding the amino acid which forms the C-terminal end to a carrier, the step-wise synthesis of the desired amino acid sequence starting at the C-terminal end, subsequently cleaving this from the carrier and coupling the resulting product a marker molecule, to a specific solid phase binding molecule, a solid phase or to a carrier molecule which is characterized in that at the position of at least one peptide bond of the natural epitope sequence a non-natural amino acid $NH_2$-$CHR^1$-X—$CHR^2$-COOH is used for the peptide synthesis instead of the first amino acid $NH_2$—$CHR^1$—COOH and the second amino acid $NH_2$—$CHR^2$—COOH which form this peptide bond in the sequence in which $R^1$ and $R^2$ which can be the same or different form side chains of natural amino acids and X represents an atom group which is protease-stable in particular a diatomic to triatomic chain such as an —NH—CO—, —$CH_2$—$CH_2$—, —CH═CH—, —NH—$CH_2$—, $CH_2$—NH, $CH_2$—O—, O—$CH_2$—, $CH_2$—S—, —S—$CH_2$— or —$CH_2$—$CH_2$—$CH_2$ group.

If the modification is a change in an amino acid side chain or the substitution of a natural amino acid of the natural epitope by an artificial, non-natural amino acid then the production process according to the invention is characterized in that an appropriately modified amino acid is used instead of the natural amino acid belonging to the epitope. Some of these artificial amino acids are commercially available or can be synthesized by methods known to a person skilled in the art (e.g. L. Gazerro et al., Solid phase synthesis, page 403, 1990; G. Jung, Peptides 1988, Walter de Gruyter, Berlin, N.Y. 1989, page 646–648; A. Jäger, Peptides 1992, Escom Science Publisher B.V. 1993, page 47–49; R. Varrel, Peptides 1990, Escom Science Publishers B.V. 1991, page 642–664, page 393–394, page 385–386, page 370–371).

Specifically, in order to synthesize the amino acid sequence the C-terminal end of an amino acid is linked via its carboxyl group to an insoluble polymer that can be readily filtered and then the peptide chain is synthesized stepwise starting at the C-terminal end. For this purpose an N-protected amino acid is reacted with a reactive group of the polymer. The N-α protecting group is removed from the amino acid covalently anchored to the carrier material and the resulting amino acyl polymer is reacted with the next N-protected amino acid. The N-α protecting group is removed from the dipeptide covalently bound to the carrier and the resulting amino-acyl polymer is reacted with the next N-protected amino acid. All excess reagents and by-products are removed by simple filtration. Once the desired modified peptide sequence has been synthesized in this manner, the covalent bond between the C-terminal amino acid and the anchor group of the polymeric carrier is cleaved. The insoluble carrier is removed from the peptide which is present in the solution by simple filtration. The peptide is purified by means of chromatographic methods. The coupling of the peptide to a solid phase, to a carrier molecule, to a specific solid phase binding site or to a label is carried out according to known methods and preferably at the N-terminal end of the peptide sequence. Biotinylation can be carried out for example according to PNAS USA 80, 1983, 4045. A preferred biotinylation agent is biotinylaminocaproic acid-N-hydroxysuccinimide ester. These groups can also already be introduced at the N-terminus of the modified amino acid sequence at the end of the solid phase synthesis.

EXAMPLE 1

Procedure for an immunoassay using biotinylated binding substances according to the invention against antibodies which are directed against the core-epitope of the HCV virus.

In the binding substances that were used one or several CO—NH peptide binding groups were replaced according to the invention (core2mI-core2mVI) compared to the natural epitope "core2m".

20 μl serum was placed in each case in streptavidin-coated ES 22 tubes from the Boehringer Mannheim Company (negative serum, positive serum, positive sera A-C). Then 1000 μl peptide solution (core 2m or core 2m I-VII concentration 100 ng/ml in potassium phosphate buffer 40 mmol/l, pH 7.0) was added by pipette and allowed to stand for 60 min in an ES 22 instrument from the Boehringer Mannheim Company. After 60 min incubation the peptide/serum solution is removed by pipette and the tubes are washed with test wash solution: 40 mmol/l potassium phosphate buffer, pH 7.0. Then 1000 μl peroxidase conjugate solution (peroxidase conjugated to an anti Fcγ antibody, 0.5 U/ml) is added by pipette and incubated for a further 60 min. The conjugate solution is removed by pipette and the tube is washed with washing solution. Afterwards 1000 μl ABTS solution (1.9 mmol/l) is added by pipette and it is incubated for a further 60 min. After 60 min incubation the solution is pipetted from the tube into a photometer and measured at 405 nm. Table 1 shows the relative reactivities of the artificial epitopes core2mI-VI compared to the natural epitope (core2m). The reactivities are derived from the measured result of the immunoassay relative to a standard curve. Despite the modification the artificial epitopes bind specifically and selectively (for example core2m I).

TABLE 1

| Peptide | Sequence | HPLC RT | HPLC integral | rel. concentration used | pos. control rel.reactivity | serum A rel.reactivity | serum B rel.reactivity | Serum C rel.reactivity |
|---|---|---|---|---|---|---|---|---|
| core2m | Bi-XUZUPQDVKFPGGGQIVGGV (SEQ ID NO: 14) | 38.264 | 3001014 | 100 | 1.140 | 1.310 | 1.170 | 1.140 |
| core2mVI | Bi-XUZUPQDVKFP4 QIV3 V (SEQ ID NO: 15) | 43.618 | 463511 | 15 | 0.360 | 0.207 | 0.330 | |
| core2mV | Bi-XUZUPQDVKFP5 QIVGG V (SEQ ID NO: 16) | 39.742 | 773020 | 26 | 0.360 | 0.160 | 0.232 | |
| core2mIV | Bi-XUZUPQDVKFP4 QIVGG V (SEQ ID NO: 17) | 42.821 | 1231484 | 41 | 0.370 | 0.250 | 0.210 | |
| core2mIII | Bi-XUZUPQDVKFP1 GQIVGG V (SEQ ID NO: 18) | 39.033 | 1512285 | 50 | 0.766 | 0.478 | 0.563 | |
| core2mII | Bi-XUZUPQDVKFPG1 QIVGG V (SEQ ID NO: 19) | 38.571 | 1762031 | 59 | 0.680 | 0.308 | 0.547 | |
| core2mI | Bi-XUZUPQDVKFPGGGQIVI V (SEQ ID NO: 20) | 38.822 | 1162908 | 39 | 1.140 | 0.621 | 0.959 | |

U = B-ala
X = tert.butyloxycarbonyl-lysine
Z = ε-aminocaproic acid
1 = aminoisobutyric acid
2 = γ-aminobutyric acid
3 = aminovaleric acid
4 = aminooctanoic acid
5 = aminotriethylene glycol Relative Reactivity The relative concentration used of the peptide antigens I-VI was derived from their HPLC integrals. The reactivity of the antigens I-VI was determined relative to the reference antigen core2m at the same concentration.

EXAMPLE 2

Experimental procedure for core2m digestion with pancreatin.

Firstly core2m solutions were prepared in distilled water at an approximate c=1–3 mg/ml. These solutions were injected into the analytical HPLC (injection volume=40 μl).

These solutions were now diluted such that the area had to be 40 000 when injected again into the HPLC. e.g. Area of the core2m IV solution was 600 000 on the analytical HPLC for an injection volume of 40 μl. Now two parts of this solution are diluted with one part of distilled water.

In each case 200 μl of these adjusted core2m solutions were admixed with 50 μl pancreatin solution (c=1 mg/ml).

A sample of these solutions was injected into the analytical HPLC after 55 min and after 125 min. As a reference a 200 μl sample of each core2m solution was admixed with 50 μl distilled water and injected into the analytical HPLC.

The percentage degradation of the respective peptide can be determined from the areas of the peptide peaks in the analytical HPLC.

Table 2 shows the percentage resistance of the individual epitope sequences towards protease degradation after 55 min and 125 min in %. Whereas the natural epitope "core2m" is completely degraded (0% resistance) the artificial epitopes core2m I-VI are considerably more resistant to proteases.

TABLE 2

HCV core2m stress with pancreatin
Core2m solutions were adjusted to HPLC areas of 400 000 in 40 μl injection volume.
Pancreatin solution c = 1 mg/ml in H₂O
200 μl of the adjusted core2m solution was allowed to react with 50 μl pancreatin solution

| Sample | Sequence | Area before | % | Area after 55 min | % | Area after 125 min | % |
|---|---|---|---|---|---|---|---|
| core2m | Bi-XUZUPQDVKFPGGGQIVGGV (SEQ ID NO: 14) | 3163895 | 100 | 0 | 0 | 0 | 0 |
| core2mI | Bi-XUZUPQDVKFPGGGQIVI V (SEQ ID NO: 20) | 3240090 | 100 | 3252704 | 100 | 2460332 | 76 |
| core2mII | Bi-XUZUPQDVKFPGI QIVGGV (SEQ ID NO: 21) | 3114243 | 100 | 561742 | 18 | 110690 | 4 |
| core2mIII | Bi-XUZUPQDVKFPI GQIVGGV (SEQ ID NO: 22) | 3265196 | 100 | 657676 | 20 | 135624 | 4 |
| core2mIV | Bi-XUZUPQDVKFP4 QIVGGV (SEQ ID NO: 17) | 3415399 | 100 | 3057359 | 90 | 2715127 | 80 |
| core2mV | Bi-XUZUPQDVKFP2 QIVGGV (SEQ ID NO: 23) | 2992631 | 100 | 2142962 | 72 | 765326 | 26 |
| core2mVI | Bi-XUZUPQDVKFP4 QIVI V (SEQ ID NO: 24) | 366701 | 100 | 2551154 | 69 | 1453596 | 39 |

EXAMPLE 3

Synthesis Of The HCV Antigen Core2m I Which Is Stable In Serum

The antigen was synthesized by means of Fmoc (fluorenyl-methoxycarbonyl) solid phase peptide synthesis using a SMPS 350 peptide synthesizer from the Zinsser Analytics Company on 15 mg 4-(2',4'-dimethoxyphenyl-Fmoc-aminomethyl)-phenoxy resin SA-5030 from the Advanced Chemtech Company with a loading of 0.52 mmol/g. Of the following N-Fmoc amino acid derivatives 90 μmol of each together with 90 μmol 1-hydroxybenzotriazol in 270 μl dimethylformamide and 105 μl of a dimethylformamide solution of 90 μmol N,N-diisopropylcarbodiimide were coupled twice in succession to the solid phase-bound peptide to be synthesized: valine δ-aminovaleric acid, valine, glycine, glycine, glycine, proline, phenyl-alanine, lysine (tert. butyloxycarbonyl), aspartic acid (tert. butyl ester), glutamine (trityl), proline, β-alanine, ε-aminocaproic acid, β-alanine, tert. butyloxycarbonyl-lysine, dimethoxytritylbiotin. The coupling times are 40 and 50 minutes. The cleavage period of the Fmoc protecting group was carried out after each double coupling using 600 μl of a 50% solution of piperidine in dimethylformamide. The cleavage period is 20 min. The washing steps are carried out eight times after each of the reaction steps using 700 μl dimethylformamide in each case. The peptide is released by treating the resin from which the solvent has been removed by filtration with 750 μl of a mixture of 90% trifluoroacetic acid, 3% thioanisol, 3% ethanedithiol and 3% thiocresol within 20 minutes and subsequently for 140 minutes. The product is precipitated by adding 15 ml cold diisopropyl ether to the combined filtrate and isolated by filtration. The residue is dissolved in 3 ml 50% acetic acid and lyophilized. The lyophilization process is repeated twice. 17 mg crude material of a purity of 94% according to reverse phase HPLC is obtained (LSIMS: M-H+; matrix: mNBA, acceleration voltage: 6 kV).

EXAMPLE 4

Synthesis Of A Tetrameric HCV Vaccine Component With Increased Resistance Towards Proteases:

The vaccine is composed of a B cell epitope of the HCV antigen (HCV core 18-33) coupled to a T cell epitope from an Epstein Barr virus (EBV LMP 43-53) in which a glycine-glycine peptide bond of the natural epitope is replaced in both epitopes by a $CH_2$—$CH_2$ group (corresponding to the incorporation of a δ aminovaleric acid).

The synthetic vaccine was synthesized by means of Fmoc (fluorenylmethoxycarbonyl)-solid phase peptide synthesis using a SMPS 350 peptide synthesizer from the Zinsser Analytics Company on 15 mg 4-(2',4'dimethoxyphenyl-Fmoc-aminomethyl)-phenoxy resin SA 5030 from the Advanced Chemtech Company with a loading of 0.22 mmol/g. Of the following N-Fmoc amino acid derivatives 90 μmol of each together with 90 μmol 1-hydroxybenzotriazol in 270 μl dimethyl-formamide and 105 μl of a dimethylformamide solution of 90 μmol N,N-diisopropylcarbodiimide were coupled twice in succession to the solid phase-bound peptide to be synthesized: Nε-Fmoc lysine, Nε-Fmoc lysine, β-alanine, β-alanine, leucine, leucine, alanine, δ-aminovaleric acid, threonine (tert.butyl ester), tryptophan, aspartic acid (tert.butyl ester), serine (tert. butyl ester), methionine, valine, valine, δ-aminovaleric acid, valine, isoleucine, glutamine (trityl), glycine, δ-aminovaleric acid, proline, phenylalanine, lysine (tert. butyloxycarbonyl), valine, aspartic acid (tert. butyl ester), glutamine (trityl), proline, acetic acid. The coupling times are 40 and 50 minutes. The cleavage period of the Fmoc protecting group is carried out after each double coupling using 600 μl of a 50% solution of piperidine in dimethyl-formamide. The cleavage period is 20 min. The washing steps are carried out eight times after each of the reaction steps using 700 μl dimethylformamide in each case. The peptide is released by treating the resin from which the solvent has been removed by filtration with 750 μl of a mixture of 90% trifluoroacetic acid, 3% thioanisol, 3% ethanedithiol and 3% thiocresol within 20 minutes and subsequently for 140 minutes. The product is precipitated by adding 15 ml cold diisopropyl ether to the combined filtrate and isolated by filtration. The residue is dissolved in 3 ml 50% acetic acid and lyophilized. The lyophilization process is repeated twice. 13 mg crude material of a purity of 42% according to reverse phase HPLC is obtained 4 mg of which are purified by means of preparative reverse phase HPLC. Yield: 0.7 mg (LSIMS: M-H+; matrix: mNBA, acceleration voltage: 6 kV).

EXAMPLE 5

BRIEF DESCRIPTION OF THE DRAWINGS

Reactivity of various side-chain modified binding substances according to the invention (mimetopes) of the HCV epitope "core 1" ["12 D1" in table 3 and FIGS. 1 and 2] and of peptide bond-modified epitopes of the HCV epitope "core2" ["1B2" in table 4 and FIG. 3].

The reactivities of the mimetopes are shown for various sera B3 to B20 compared to the standard antigen core1 (12D1) and core2 (1B2) (FIGS. 1 to 7). The sera RS and RS2 (FIGS. 1 and 2) and B112, B119, B126, B129 and B117 (FIG. 3) are negative sera. FIG. 1 shows that negative sera are specifically detected as such using side-chain modified mimetopes.

The mimetopes exhibit comparable reactivities to natural epitopes and in some cases even higher reactivities.

FIGS. 4 to 7 show that when monitoring sera of recently infected persons the serum conversion can be detected with mimetopes at a comparatively early stage or even earlier.

The reactivities were determined analogously to example 1.

EXAMPLE 6

Immunoassay procedure using biotinylated binding substances according to the invention against antibodies directed against the gp32 epitope of the HIV virus.

In the binding substances used (gp32-4 to gp32-20) one or several natural amino acids were replaced by unnatural amino acids 1–7 (table 5) compared to the natural epitope (HIV gp32Bi "standard sequence") .

The immunoassay was carried out analogously to example 1 with 5 different sera. FIG. 8 shows the relative reactivities of the various binding substances compared to the natural epitope. In some cases it was even possible to measure a higher reactivity.

TABLE 3

HCV mimetopes of Core 1
(12D1: KKNKRNTNRR) (SEQ ID NO: 25)

| Mimetope | Structure | Description | Evaluation |
|---|---|---|---|
| 30D2 | TlyTlyAsnTlyArgAsnThrAsnArgArg (SEQ ID NO: 26) | side-chain mimetope K → thialysine (Tly) | s. FIG. 1 |
| 30D1 | LysLysCsaLysArgCsaThrCsaArgArg (SEQ ID NO: 27) | side-chain mimetope N → cysteine sulfonamide (Csa) | s. FIG. 1 |
| Cl-canavanine | LysLysAsnLysCanAsnThrAsnCanCan (SEQ ID NO: 28) | side-chain mimetope R → canavanine (Can) | s. FIG. 1 |

TABLE 4

HCV Mimetopes of Core 2
(1B2: PQDVKFPGGGQIVGGV) (SEQ ID NO: 29)

| Mimetope | Structure | Description | Evaluation |
|---|---|---|---|
| C2R1 | PQDVKFPGGψGQIVGGV (SEQ ID NO: 30) | peptide binding mimetope G-G → G(ψNH—CO)G | s. FIG. 2,3,4,5,6 and 7 |
| C2R2 | PQDVKFPGGGQIVGψGV (SEQ ID NO: 31) | peptide binding mimetope G-G → G(ψNH—CO)G | s. FIG. 2,3,4,5,6 and 7 |
| C2psiGGG | PQDVKFPGψGψGQIVGGV (SEQ ID NO: 32) | peptide binding mimetope G-G → G(ψNH—CO)G | s. FIG. 3 |
| C2psipsi | PQDVKFPGGψGQIVGψGV (SEQ ID NO: 33) | peptide binding mimetope G-G → G(ψNH—CO)G | s. FIG. 3 |

TABLE 5

Mimetopes HCV gp32

| | S | W | G | C | A | F | R | Q | V | C | H | T | T | Standard sequence (SEQ ID NO: 1) |
|---|---|---|---|---|---|---|---|---|---|---|---|---|---|---|
| Q | S | W | A | C | 7 | F | R | Q | L | C | H | T | T | gp32-4 (SEQ ID NO: 2) |
| N | S | W | G | C | A | F | R | Q | 1 | C | H | T | T | gp32-6 (SEQ ID NO: 3) |
| N | S | 2 | G | C | A | F | R | Q | V | C | H | T | T | gp32-7 (SEQ ID NO: 4) |
| N | S | W | G | C | A | F | 3 | Q | V | C | H | T | T | gp32-8 (SEQ ID NO: 5) |
| N | S | 4 | G | C | A | F | R | Q | V | C | H | T | T | gp32-9 (SEQ ID NO: 6) |
| N | S | W | G | C | A | 5 | R | Q | V | C | H | T | T | gp32-10 (SEQ ID NO: 7) |
| N | S | W | G | C | A | 6 | R | Q | V | C | H | T | T | gp32-11 (SEQ ID NO: 8) |
| N | S | W | G | C | A | 6 | 3 | Q | V | C | H | T | T | gp32-15 (SEQ ID NO: 9) |
| N | S | W | G | C | A | 6 | 3 | Q | 1 | C | H | T | T | gp32-16 (SEQ ID NO: 10) |
| N | S | W | G | C | A | F | R | 8 | L | C | H | T | T | gp32-18 (SEQ ID NO: 11) |

TABLE 5-continued

Mimetopes HCV gp32

Figure 1:
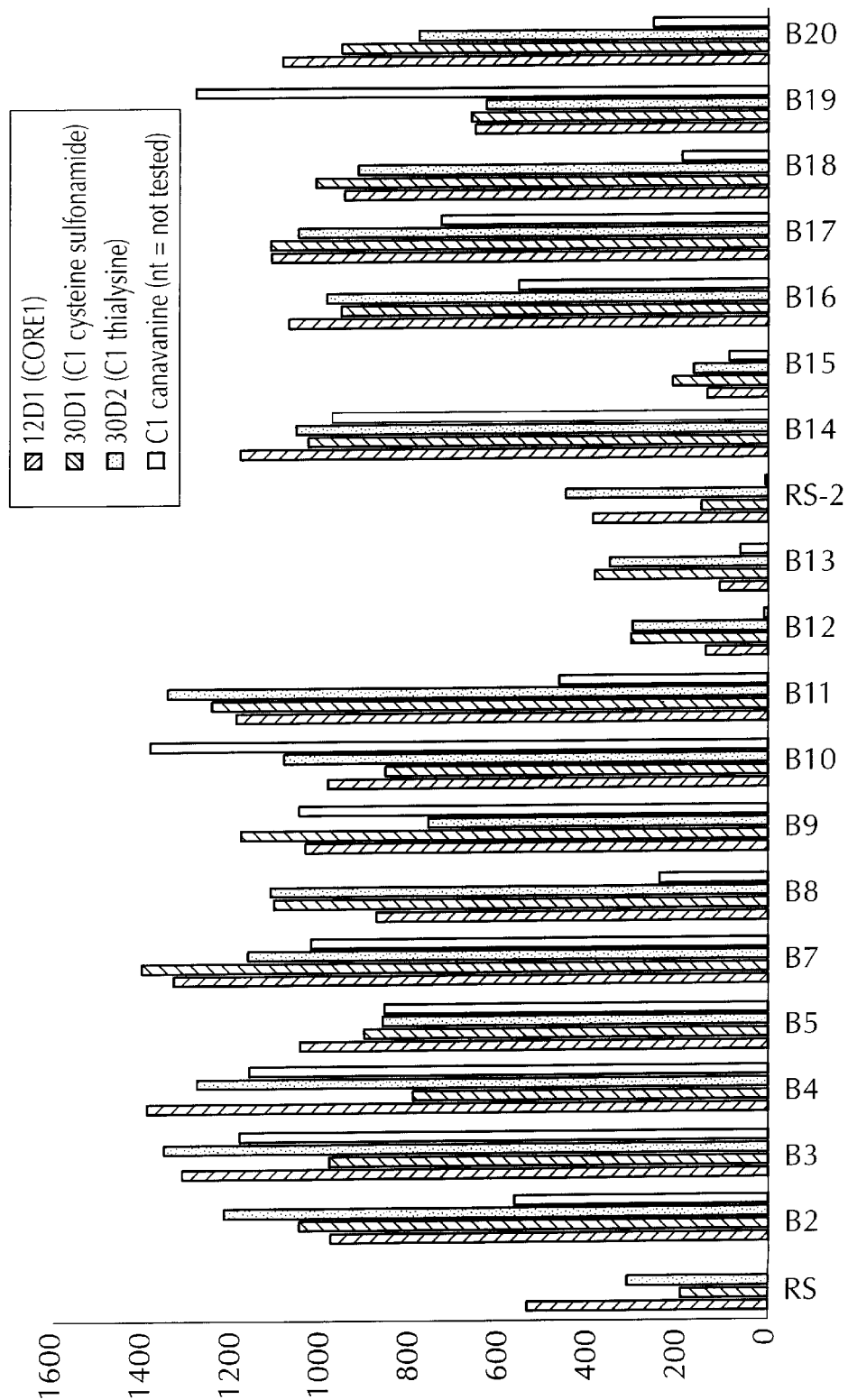
Figure 2:
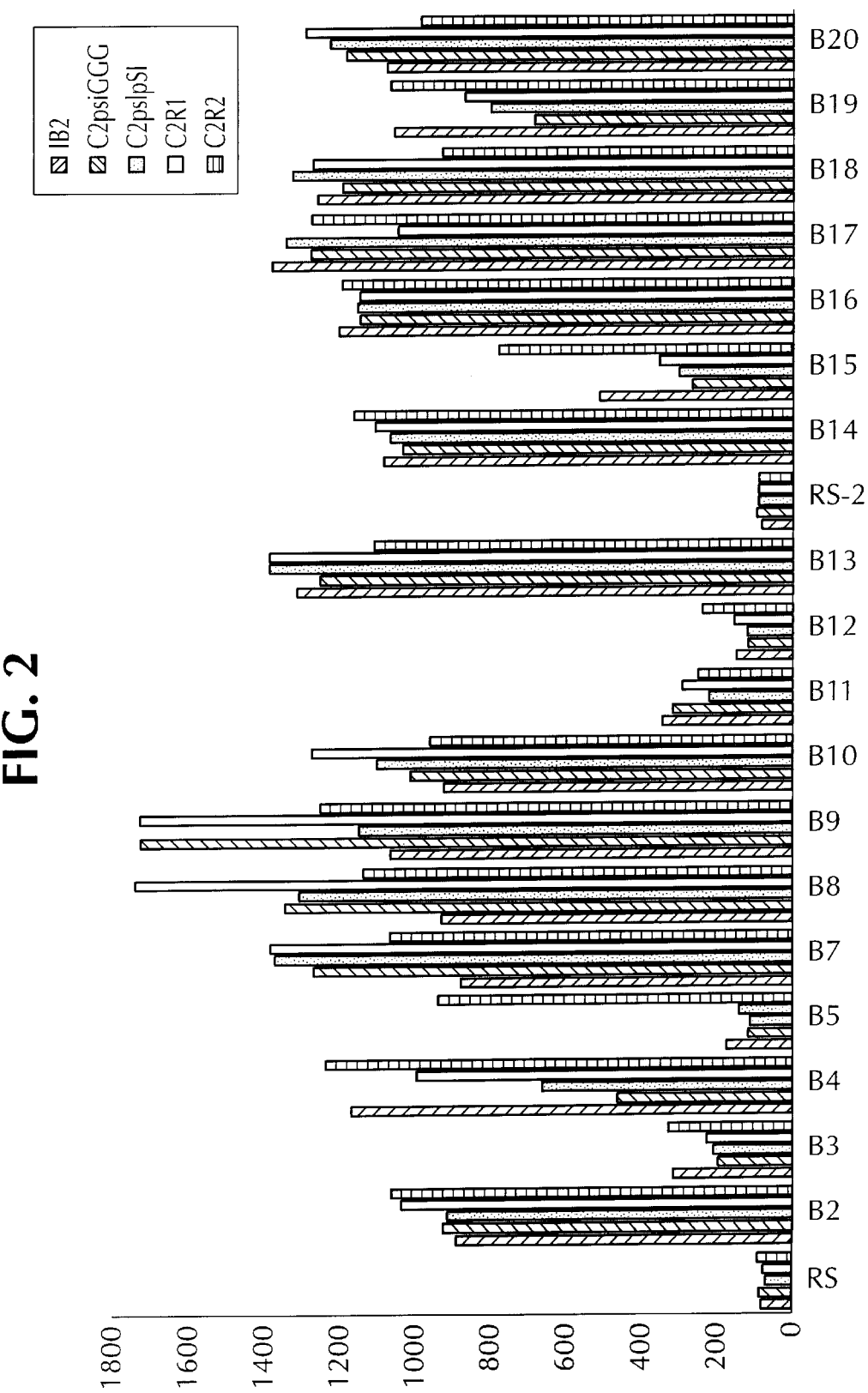
Figure 3:
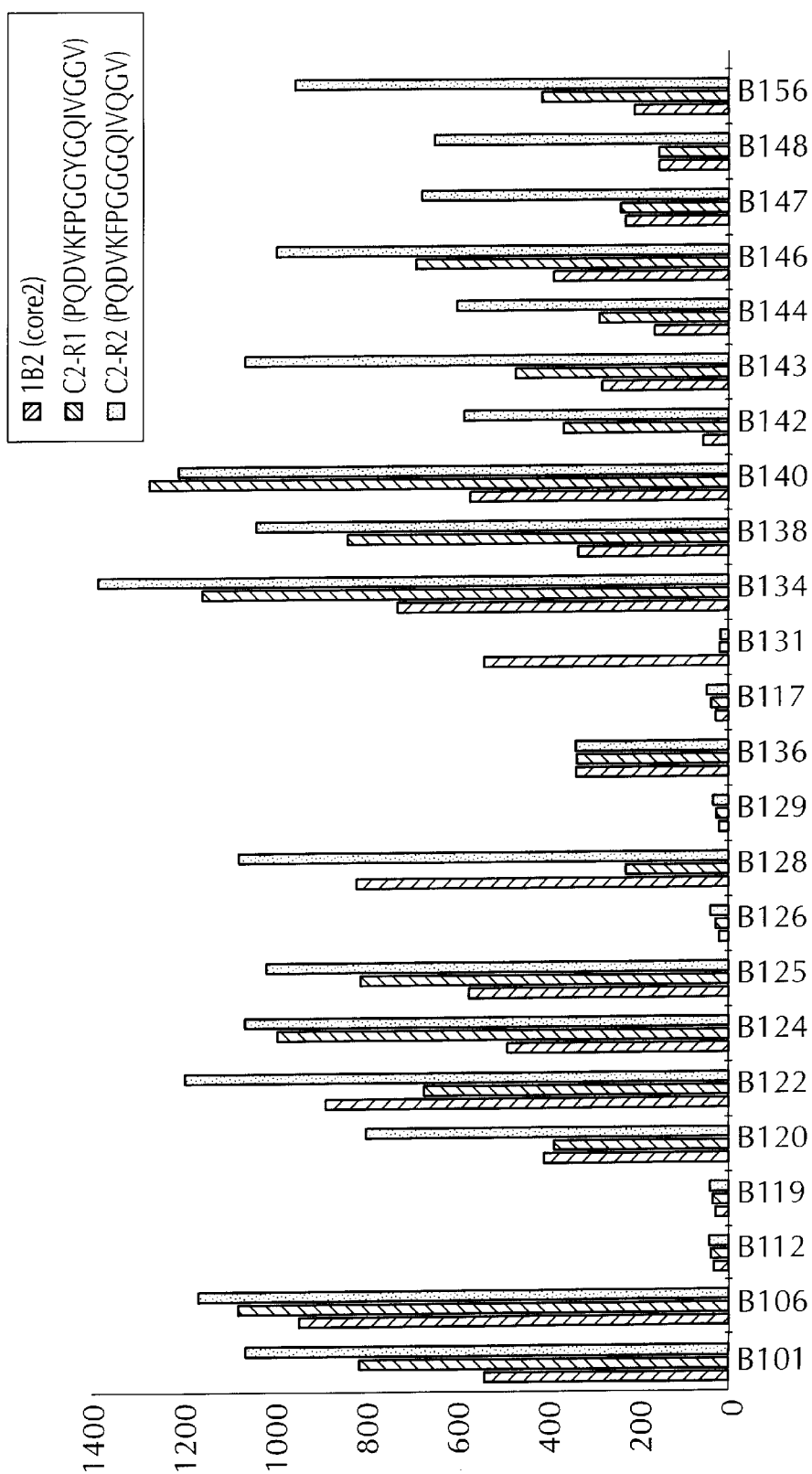
Figure 4:
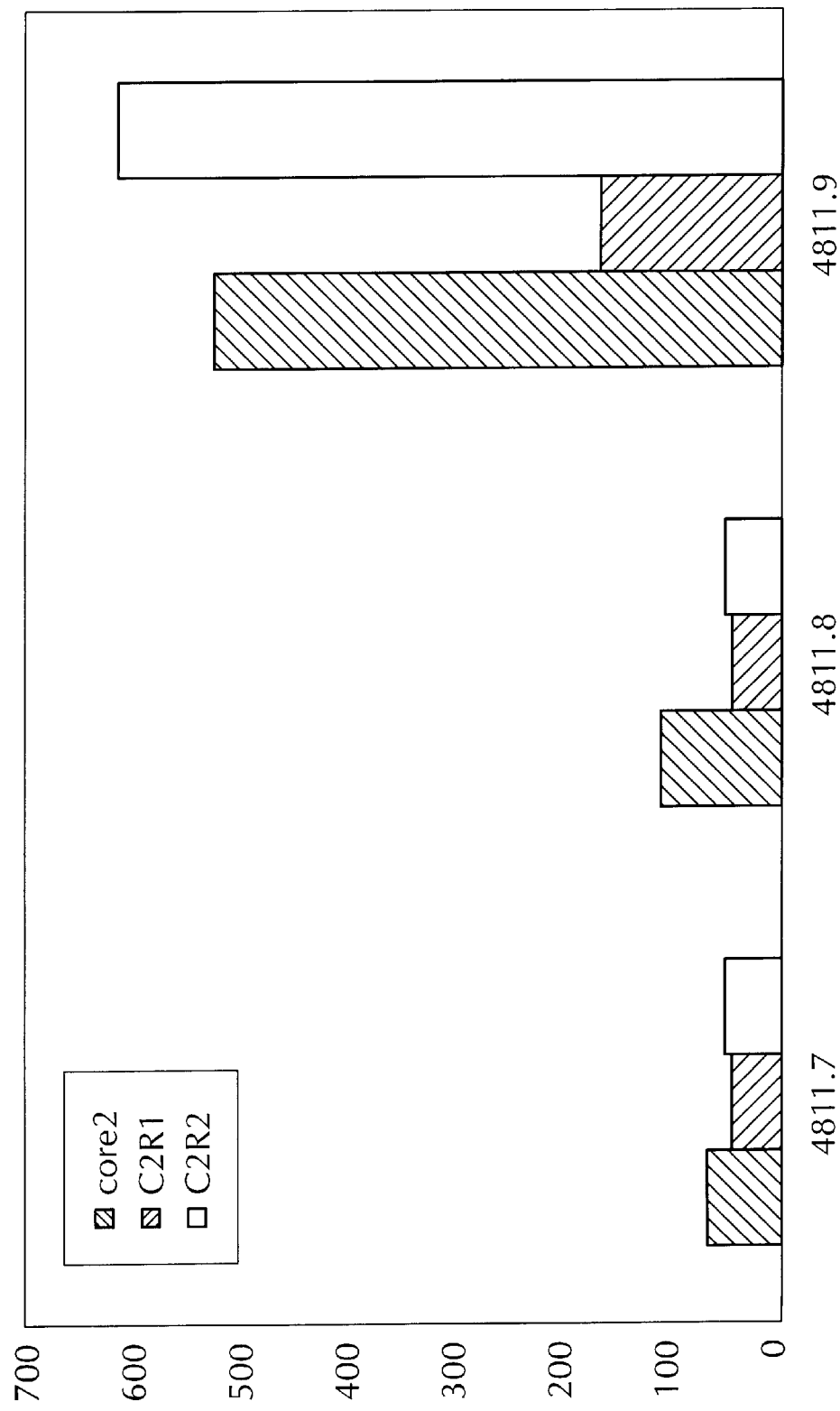
Figure 5:
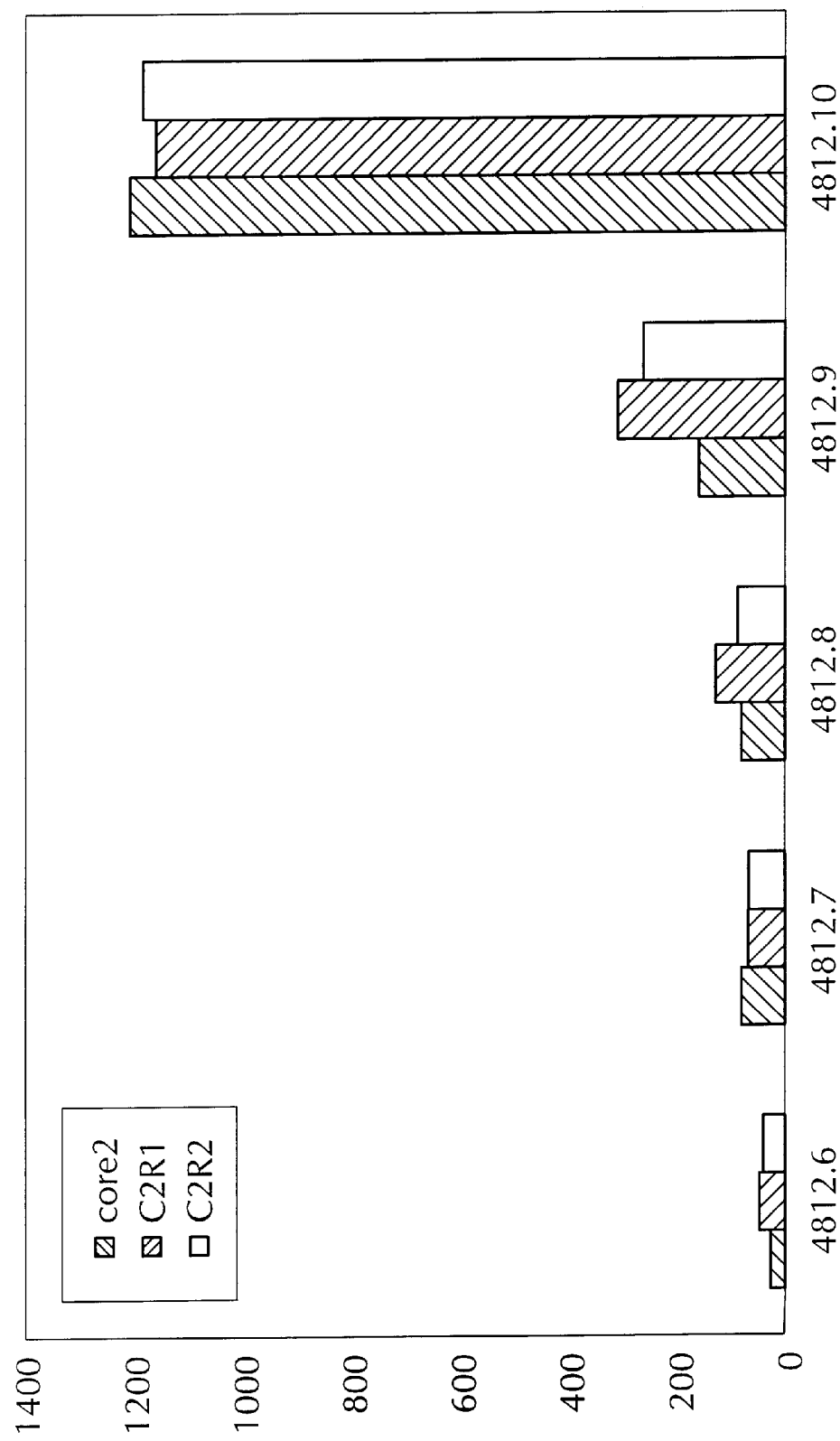
Figure 6:
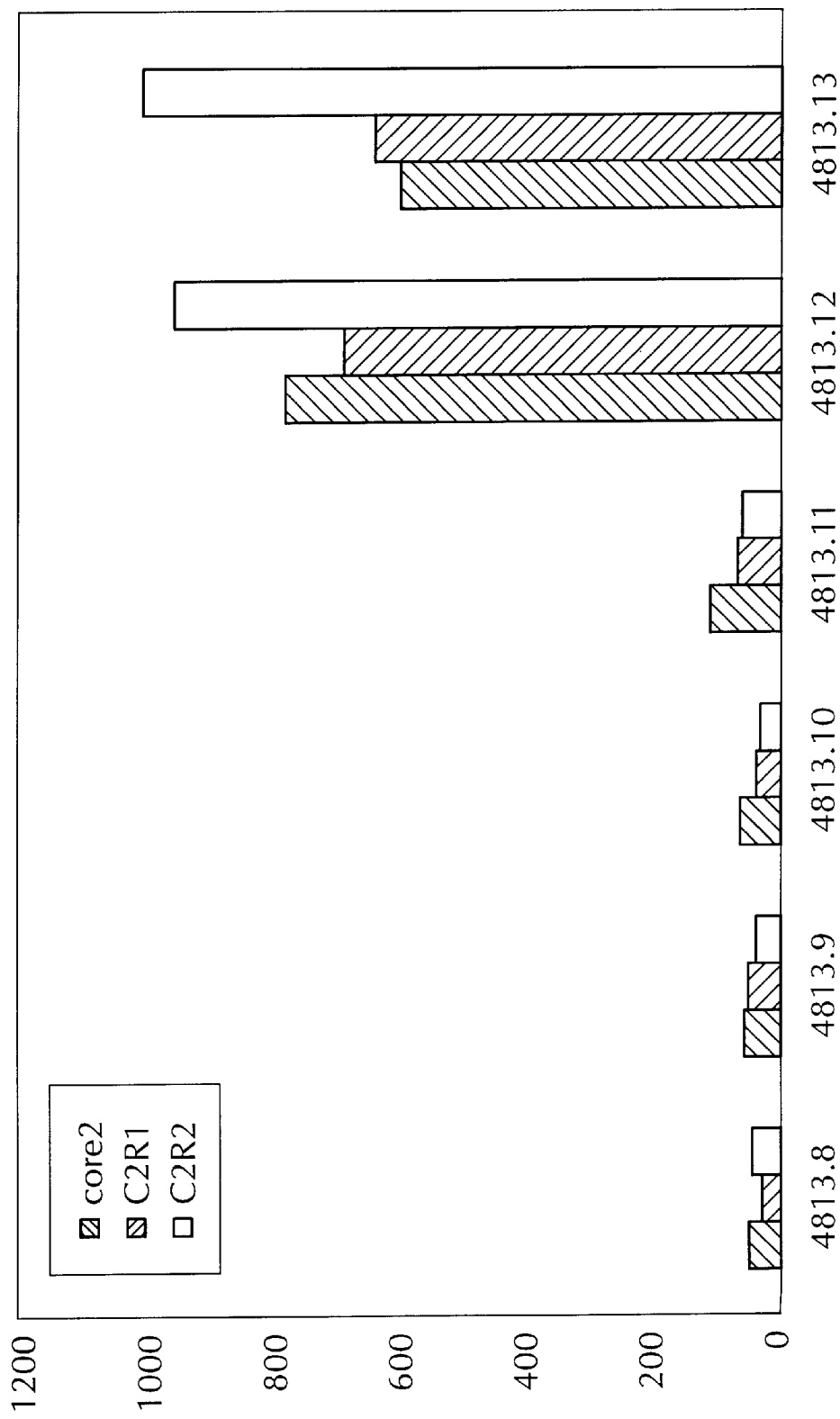
Figure 7:
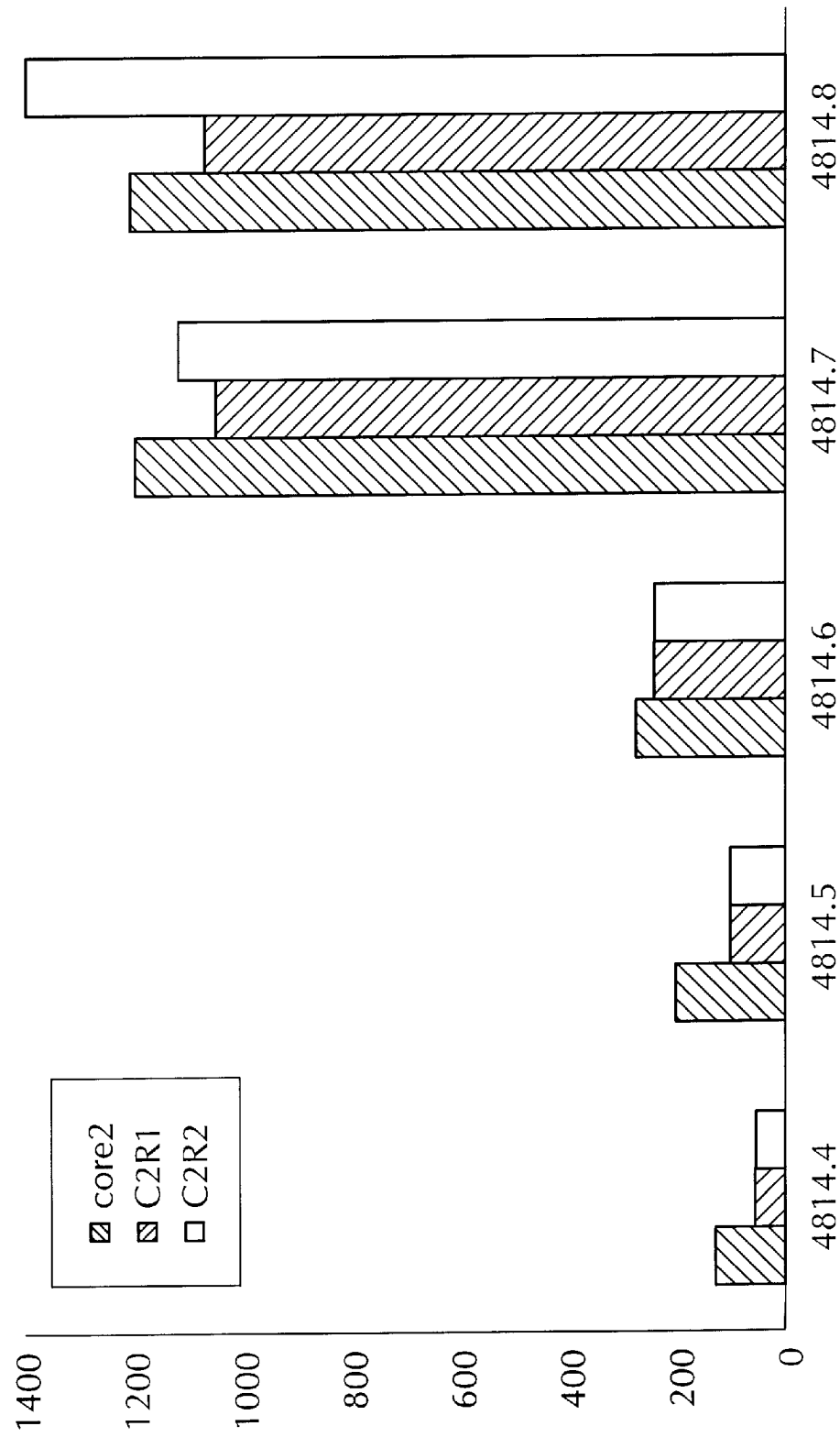

| S | W | G | C | A | F | R | Q | V | C | H | T | T | Standard sequence (SEQ ID NO: 1) |
|---|---|---|---|---|---|---|---|---|---|---|---|---|---|
| Q | T | W | G | C | A | 6 | 3 | Q | V | C | H | S | S | gp32-19 (SEQ ID NO: 12) |
| Q | T | W | G | C | G | 6 | 3 | 8 | L | C | H | S | S | gp32-20 (SEQ ID NO: 13) |

1 = norvaline
2 = β-1-napthylanine
3 = canavanine sulfate
4 = H-β-3-benzothienyl-Ala-OH
5 = p-fluor-Phe-OH
6 = homo-Phe-OH
7 = α-aminobutyric acid
8 = norleucine

---

SEQUENCE LISTING (1) GENERAL INFORMATION:

(iii) NUMBER OF SEQUENCES: 33

(2) INFORMATION FOR SEQ ID NO: 1:

(i) SEQUENCE CHARACTERISTICS:
      (A) LENGTH: 13
      (B) TYPE: amino acids
      (D) TOPOLOGY: linear (ii) MOLECULE TYPE: protein (xi) SEQUENCE DESCRIPTION: SEQ ID NO: 1:

Ser Trp Gly Cys Ala Phe Arg Gln Val Cys His Thr Thr
                5                         10

(2) INFORMATION FOR SEQ ID NO: 2:

(i) SEQUENCE CHARACTERISTICS:
      (A) LENGTH: 14
      (B) TYPE: amino acids
      (D) TOPOLOGY: linear (ii) MOLECULE TYPE: protein (ix) FEATURE:
      (D) OTHER INFORMATION: The first Xaa is α-aminobutyric acid
           and the second Xaa is Nva (xi) SEQUENCE DESCRIPTION: SEQ ID NO: 2:

Gln Ser Trp Ala Cys Xaa Phe Arg Gln Xaa Cys His Thr Thr
                5                        10

(2) INFORMATION FOR SEQ ID NO: 3:

(i) SEQUENCE CHARACTERISTICS:
      (A) LENGTH: 14
      (B) TYPE: amino acids
      (D) TOPOLOGY: unknown (ii) MOLECULE TYPE: protein (ix) FEATURE:
      (D) OTHER INFORMATION: Xaa is Nva (xi) SEQUENCE DESCRIPTION: SEQ ID NO: 3:

Asn Ser Trp Gly Cys Ala Phe Arg Gln Xaa Cys His Thr Thr
                5                        10

(2) INFORMATION FOR SEQ ID NO:  4:

(i) SEQUENCE CHARACTERISTICS:
       (A) LENGTH: 14
       (B) TYPE: amino acids
       (D) TOPOLOGY: linear (ii) MOLECULE TYPE: protein (ix) FEATURE:
       (D) OTHER INFORMATION:  Xaa is β-1-napthylanine (xi) SEQUENCE DESCRIPTION:    SEQ ID NO: 4:

Asn Ser Xaa Gly Cys Ala Phe Arg Gln Val Cys His Thr Thr
                5                   10

(2) INFORMATION FOR SEQ ID NO:  5:

(i) SEQUENCE CHARACTERISTICS:
       (A) LENGTH: 14
       (B) TYPE: amino acids
       (D) TOPOLOGY: linear (ii) MOLECULE TYPE: protein (ix) FEATURE:
       (D) OTHER INFORMATION:  Xaa is canavanine sulfate (xi) SEQUENCE DESCRIPTION:    SEQ ID NO: 5:

Asn Ser Trp Gly Cys Ala Phe Xaa Gln Val Cys His Thr Thr
                5                   10

(2) INFORMATION FOR SEQ ID NO:  6:

(i) SEQUENCE CHARACTERISTICS:
       (A) LENGTH: 14
       (B) TYPE: amino acids
       (D) TOPOLOGY: linear (ii) MOLECULE TYPE: protein (ix) FEATURE:
       (D) OTHER INFORMATION: Xaa is H-β-3-benzothientyl-Alanine (xi) SEQUENCE DESCRIPTION:    SEQ ID NO: 6:

Asn Ser Xaa Gly Cys Ala Phe Arg Gln Val Cys His Thr Thr
                5                   10

(2) INFORMATION FOR SEQ ID NO:  7:

(i) SEQUENCE CHARACTERISTICS:
       (A) LENGTH: 14
       (B) TYPE: amino acids
       (D) TOPOLOGY: linear (ii) MOLECULE TYPE: protein (ix) FEATURE:
       (D) OTHER INFORMATION:  Xaa is p-fluor-Phenylalanine (xi) SEQUENCE DESCRIPTION:    SEQ ID NO: 7:

Asn Ser Trp Gly Cys Ala Xaa Arg Gln Val Cys His Thr Thr
                5                   10

(2) INFORMATION FOR SEQ ID NO:  8:

(i) SEQUENCE CHARACTERISTICS:
       (A) LENGTH: 14
       (B) TYPE: amino acids
       (D) TOPOLOGY: linear

```
      (ii) MOLECULE TYPE: protein (ix) FEATURE:
           (D) OTHER INFORMATION:  Xaa is homo-Phenylalanine (xi) SEQUENCE DESCRIPTION:     SEQ ID NO: 8:

Asn Ser Trp Gly Cys Ala Xaa Arg Gln Val Cys His Thr Thr
              5                  10

(2) INFORMATION FOR SEQ ID NO:    9:

(i) SEQUENCE CHARACTERISTICS:
          (A) LENGTH: 14
          (B) TYPE: amino acids
          (D) TOPOLOGY: linear (ii) MOLECULE TYPE: protein (ix) FEATURE:
           (D) OTHER INFORMATION: The first Xaa is homo-Phenylalanine and
               the second Xaa is canavanine sulfate (xi) SEQUENCE DESCRIPTION:     SEQ ID NO: 9:

Asn Ser Trp Gly Cys Ala Xaa Xaa Gln Val Cys His Thr Thr
              5                  10

(2) INFORMATION FOR SEQ ID NO:    10:

(i) SEQUENCE CHARACTERISTICS:
          (A) LENGTH: 14
          (B) TYPE: amino acids
          (D) TOPOLOGY: linear (ii) MOLECULE TYPE: protein (ix) FEATURE:
           (D) OTHER INFORMATION: The first Xaa is homo-Phenylalanine;
               the second Xaa is canavanine sulfate; and the third Xaa is
               Nva (xi) SEQUENCE DESCRIPTION:     SEQ ID NO: 10:

Asn Ser Trp Gly Cys Ala Xaa Xaa Gln Xaa Cys His Thr Thr
              5                  10

(2) INFORMATION FOR SEQ ID NO:    11:

(i) SEQUENCE CHARACTERISTICS:
          (A) LENGTH: 14
          (B) TYPE: amino acids
          (D) TOPOLOGY: linear (ii) MOLECULE TYPE: protein (ix) FEATURE:
           (D) OTHER INFORMATION:  Xaa is Nle (xi) SEQUENCE DESCRIPTION:     SEQ ID NO: 11:

Asn Ser Trp Gly Cys Ala Phe Arg Xaa Leu Cys His Thr Thr
              5                  10

(2) INFORMATION FOR SEQ ID NO:    12:

(i) SEQUENCE CHARACTERISTICS:
          (A) LENGTH: 14
          (B) TYPE: amino acids
          (D) TOPOLOGY: linear (ii) MOLECULE TYPE: protein (ix) FEATURE:
```

(D) OTHER INFORMATION: The first Xaa is homo-Phenylalanine and
                the second Xaa is canavanine sulfate (xi) SEQUENCE DESCRIPTION:     SEQ ID NO: 12:

Gln Thr Trp Gly Cys Ala Xaa Xaa Gln Val Cys His Ser Ser
                 5                   10

(2) INFORMATION FOR SEQ ID NO:     13:

(i) SEQUENCE CHARACTERISTICS:
        (A) LENGTH: 14
        (B) TYPE: amino acids
        (D) TOPOLOGY: linear (ii) MOLECULE TYPE: protein (ix) FEATURE:
        (D) OTHER INFORMATION: The first Xaa is homo-Phenylalanine;
            the second Xaa is canavanine sulfate; and the third Xaa is
            Nle (xi) SEQUENCE DESCRIPTION:     SEQ ID NO: 13:

Gln Thr Trp Gly Cys Gly Xaa Xaa Xaa Leu Cys His Ser Ser
                 5                   10

(2) INFORMATION FOR SEQ ID NO:     14:

(i) SEQUENCE CHARACTERISTICS:
        (A) LENGTH: 20
        (B) TYPE: amino acids
        (D) TOPOLOGY: linear (ii) MOLECULE TYPE: protein (ix) FEATURE:
        (D) OTHER INFORMATION: The first Xaa is Tertbutyloxycarbonyl-
            lysine; the second Xaa is bAla; the third Xaa is Acp; and
            the fourth Xaa is bAla The label dimethoxytritylbiotin is
            coupled to the free amino group of the first Xaa.

(xi) SEQUENCE DESCRIPTION:     SEQ ID NO: 14:

Xaa Xaa Xaa Xaa Pro Gln Asp Val Lys Phe Pro Gly Gly Gly Gln Ile
                 5                   10                  15

Val Gly Gly Val
             20

(2) INFORMATION FOR SEQ ID NO:     15:

(i) SEQUENCE CHARACTERISTICS:
        (A) LENGTH: 17
        (B) TYPE: amino acids
        (D) TOPOLOGY: linear (ii) MOLECULE TYPE: protein (ix) FEATURE:
        (D) OTHER INFORMATION: The first Xaa is tertbutyloxycarbonyl-
            lysine; the second Xaa is bAla; the third Xaa is Acp; the
            fourth Xaa is bAla; the fifth Xaa is aminooctanoic acid;
            and the sixth Xaa is aminovaleric acid. The label
            dimethoxytritylbiotin is coupled to the free amino group
            of the first Xaa.

(xi) SEQUENCE DESCRIPTION:     SEQ ID NO: 15:

Xaa Xaa Xaa Xaa Pro Gln Asp Val Lys Phe Pro Xaa Gln Ile Val Xaa
                 5                   10                  15

Val (2) INFORMATION FOR SEQ ID NO:     16:

```
        (i) SEQUENCE CHARACTERISTICS:
            (A) LENGTH: 18
            (B) TYPE: amino acids
            (D) TOPOLOGY: linear (ii) MOLECULE TYPE: protein (ix) FEATURE:
            (D) OTHER INFORMATION: The first Xaa is tertbutyloxycarbonyl-
                lysine; the second Xaa is bAla; the third Xaa is Acp; the
                fourth Xaa is bAla; and the fifth Xaa is aminotriethylene
                glycol. The label dimethoxytritylbiotin is coupled to the
                free amino group of the first Xaa.

(xi) SEQUENCE DESCRIPTION:     SEQ ID NO: 16:

Xaa Xaa Xaa Xaa Pro Gln Asp Val Lys Phe Pro Xaa Gln Ile Val Gly
                 5                  10                  15

Gly Val (2) INFORMATION FOR SEQ ID NO:    17:

(i) SEQUENCE CHARACTERISTICS:
            (A) LENGTH: 18
            (B) TYPE: amino acids
            (D) TOPOLOGY: linear (ii) MOLECULE TYPE: protein (ix) FEATURE:
            (D) OTHER INFORMATION: The first Xaa is tertbutyloxycarbonyl-
                lysine; the second Xaa is bAla; the third Xaa is Acp; the
                fourth Xaa is bAla; and the fifth Xaa is aminooctanoic
                acid. The label dimethoxytritylbiotin is coupled to the
                free amino group of the first Xaa.

(xi) SEQUENCE DESCRIPTION:     SEQ ID NO: 17:

Xaa Xaa Xaa Xaa Pro Gln Asp Val Lys Phe Pro Xaa Gln Ile Val Gly
                 5                  10                  15

Gly Val (2) INFORMATION FOR SEQ ID NO:    18:

(i) SEQUENCE CHARACTERISTICS:
            (A) LENGTH: 19
            (B) TYPE: amino acids
            (D) TOPOLOGY: linear (ii) MOLECULE TYPE: protein (ix) FEATURE:
            (D) OTHER INFORMATION: The first Xaa is tertbutyloxycarbonyl-
                lysine; the second Xaa is bAla; the third Xaa is Acp; the
                fourth Xaa is bAla; and the Xaa is aminoisobutyric acid.
                The label dimethoxytritylbiotin is coupled to the free
                amino group of the first Xaa.

(xi) SEQUENCE DESCRIPTION:     SEQ ID NO: 18:

Xaa Xaa Xaa Xaa Pro Gln Asp Val Lys Phe Pro Xaa Gly Gln Ile Val
                 5                  10                  15

Gly Gly Val (2) INFORMATION FOR SEQ ID NO:    19:

(i) SEQUENCE CHARACTERISTICS:
            (A) LENGTH: 19
            (B) TYPE: amino acids
            (D) TOPOLOGY: linear (ii) MOLECULE TYPE: protein
```

(ix) FEATURE:
    (D) OTHER INFORMATION: The first Xaa is tertbutyloxycarbonyl-
        lysine; the Xaa is bAla; the third Xaa is Acp; the fourth
        Xaa is bAla; and the fifth Xaa is aminoisobutyric acid.
        The label dimethoxytritylbiotin is coupled to the free
        amino group of the first Xaa.

(xi) SEQUENCE DESCRIPTION: SEQ ID NO: 19:

```
Xaa Xaa Xaa Xaa Pro Gln Asp Val Lys Phe Pro Gly Xaa Gln Ile Val
                 5                   10                  15
Gly Gly Val
```

(2) INFORMATION FOR SEQ ID NO: 20:

(i) SEQUENCE CHARACTERISTICS:
        (A) LENGTH: 19
        (B) TYPE: amino acids
        (D) TOPOLOGY: linear (ii) MOLECULE TYPE: protein (ix) FEATURE:
        (D) OTHER INFORMATION: The first Xaa is tertbutyloxycarbonyl-
            lysine; the second Xaa is bAla; the third Xaa is Acp; and
            the fourth Xaa is bAla. The label dimethoxytritylbiotin is
            coupled to the free amino group of the first Xaa.

(xi) SEQUENCE DESCRIPTION: SEQ ID NO: 20:

```
Xaa Xaa Xaa Xaa Pro Gln Asp Val Lys Phe Pro Gly Gly Gly Gln Ile
                 5                   10                  15
Val Ile Val
```

(2) INFORMATION FOR SEQ ID NO: 21:

(i) SEQUENCE CHARACTERISTICS:
        (A) LENGTH: 19
        (B) TYPE: amino acids
        (D) TOPOLOGY: linear (ii) MOLECULE TYPE: protein (ix) FEATURE:
        (D) OTHER INFORMATION: The first Xaa is tertbutyloxycarbonyl-
            lysine; the second Xaa is bAla; the third Xaa is Acp; and
            the fourth Xaa is bAla. The label dimethoxytritylbiotin is
            coupled to the free amino group of the first Xaa.

(xi) SEQUENCE DESCRIPTION: SEQ ID NO: 21:

```
Xaa Xaa Xaa Xaa Pro Gln Asp Val Lys Phe Pro Gly Ile Gln Ile Val
                 5                   10                  15
Gly Gly Val
```

(2) INFORMATION FOR SEQ ID NO: 22:

(i) SEQUENCE CHARACTERISTICS:
        (A) LENGTH: 19
        (B) TYPE: amino acids
        (D) TOPOLOGY: linear (ii) MOLECULE TYPE: protein (ix) FEATURE:
        (D) OTHER INFORMATION: The first Xaa is tertbutyloxycarbonyl-
            lysine; the second Xaa is bAla; the third Xaa is Acp; and
            the fourth Xaa is bAla. The label dimethoxytritylbiotin is
            coupled to the free amino group of the first Xaa.

(xi) SEQUENCE DESCRIPTION: SEQ ID NO: 22:

```
Xaa Xaa Xaa Xaa Pro Gln Asp Val Lys Phe Pro Ile Gly Gln Ile Val
            5                   10                  15
Gly Gly Val
```

(2) INFORMATION FOR SEQ ID NO: 23:

(i) SEQUENCE CHARACTERISTICS:
        (A) LENGTH: 18
        (B) TYPE: amino acids
        (D) TOPOLOGY: linear (ii) MOLECULE TYPE: protein (ix) FEATURE:
        (D) OTHER INFORMATION: The first Xaa is tertbutyloxycarbonyl-
           lysine; the second Xaa is bAla; the third Xaa is Acp; the
           fourth Xaa is bAla; and the fifth Xaa is γ-aminobutyric
           acid. The label dimethoxytritylbiotin is coupled to the
           free amino group of the first Xaa.

(xi) SEQUENCE DESCRIPTION: SEQ ID NO: 23:

```
Xaa Xaa Xaa Xaa Pro Gln Asp Val Lys Phe Pro Xaa Gln Ile Val Gly
            5                   10                  15
Gly Val
```

(2) INFORMATION FOR SEQ ID NO: 24:

(i) SEQUENCE CHARACTERISTICS:
        (A) LENGTH: 17
        (B) TYPE: amino acids
        (D) TOPOLOGY: linear (ii) MOLECULE TYPE: protein (ix) FEATURE:
        (D) OTHER INFORMATION: The first Xaa is tertbutyloxycarbonyl-
           lysine; the second Xaa is bAla; the third Xaa is Acp; the
           fourth Xaa is bAla; and the fifth Xaa is aminooctanoic
           acid. The label dimethoxytritylbuotin is coupled to the
           free amino group of the first Xaa.

(xi) SEQUENCE DESCRIPTION: SEQ ID NO: 24:

```
Xaa Xaa Xaa Xaa Pro Gln Asp Val Lys Phe Pro Xaa Gln Ile Val Ile
            5                   10                  15
Val
```

(2) INFORMATION FOR SEQ ID NO: 25:

(i) SEQUENCE CHARACTERISTICS:
        (A) LENGTH: 10
        (B) TYPE: amino acids
        (D) TOPOLOGY: linear (ii) MOLECULE TYPE: protein (xi) SEQUENCE DESCRIPTION: SEQ ID NO: 25:

```
Lys Lys Asn Lys Arg Asn Thr Asn Arg Arg
            5                   10
```

(2) INFORMATION FOR SEQ ID NO: 26:

(i) SEQUENCE CHARACTERISTICS:
        (A) LENGTH: 10
        (B) TYPE: amino acids
        (D) TOPOLOGY: linear (ii) MOLECULE TYPE: protein (ix) FEATURE:

```
            (D) OTHER INFORMATION: The first, second, and third Xaa are
                thialysine.

(xi) SEQUENCE DESCRIPTION:      SEQ ID NO: 26:

Xaa Xaa Asn Xaa Arg Asn Thr Asn Arg Arg
                 5                  10

(2) INFORMATION FOR SEQ ID NO:    27:

(i) SEQUENCE CHARACTERISTICS:
            (A) LENGTH: 10
            (B) TYPE: amino acids
            (D) TOPOLOGY: linear (ii) MOLECULE TYPE: protein (ix) FEATURE:
            (D) OTHER INFORMATION: The first, second, and third Xaa are
                cysteine sulfonamide.

(xi) SEQUENCE DESCRIPTION:      SEQ ID NO: 27:

Lys Lys Xaa Lys Arg Xaa Thr Xaa Arg Arg
                 5                  10

(2) INFORMATION FOR SEQ ID NO:    28:

(i) SEQUENCE CHARACTERISTICS:
            (A) LENGTH: 10
            (B) TYPE: amino acids
            (D) TOPOLOGY: linear (ii) MOLECULE TYPE: protein (ix) FEATURE:
            (D) OTHER INFORMATION: The first, second, and third Xaa are
                canavanine.

(xi) SEQUENCE DESCRIPTION:      SEQ ID NO: 28:

Lys Lys Asn Lys Xaa Asn Thr Asn Xaa Xaa
                 5                  10

(2) INFORMATION FOR SEQ ID NO:    29:

(i) SEQUENCE CHARACTERISTICS:
            (A) LENGTH: 16
            (B) TYPE: amino acids
            (D) TOPOLOGY: linear (ii) MOLECULE TYPE: protein (xi) SEQUENCE DESCRIPTION:      SEQ ID NO: 29:

Pro Gln Asp Val Lys Phe Pro Gly Gly Gly Gln Ile Val Gly Gly Val
                 5                  10                  15

(2) INFORMATION FOR SEQ ID NO:    30:

(i) SEQUENCE CHARACTERISTICS:
            (A) LENGTH: 16
            (B) TYPE: amino acids
            (D) TOPOLOGY: linear (ii) MOLECULE TYPE: protein (ix) FEATURE:
            (D) OTHER INFORMATION: The first Xaa and the second Xaa are
                glycine residues wherein the -CO-NH- group between the two
                residues is replaced by an NH-CO group.

(xi) SEQUENCE DESCRIPTION:      SEQ ID NO: 30:

Pro Gln Asp Val Lys Phe Pro Gly Xaa Xaa Gln Ile Val Gly Gly Val
```

(2) INFORMATION FOR SEQ ID NO: 31:

(i) SEQUENCE CHARACTERISTICS:
        (A) LENGTH: 16
        (B) TYPE: amino acids
        (D) TOPOLOGY: linear (ii) MOLECULE TYPE: protein (ix) FEATURE:
        (D) OTHER INFORMATION: The first Xaa and the second Xaa are
            each glycine residues wherein the -CO-NH- group between
            these two residues is replaced by an NH-CO group (xi) SEQUENCE DESCRIPTION: SEQ ID NO: 31:

Pro Gln Asp Val Lys Phe Pro Gly Gly Gly Gln Ile Val Xaa Xaa Val
           5                    10                 15

(2) INFORMATION FOR SEQ ID NO: 32:

(i) SEQUENCE CHARACTERISTICS:
        (A) LENGTH: 16
        (B) TYPE: amino acids
        (D) TOPOLOGY: linear (ii) MOLECULE TYPE: protein (ix) FEATURE:
        (D) OTHER INFORMATION: The first Xaa, the second Xaa, and the
            third Xaa are each glycine residues wherein the -CO-NH
            group between the glycine residues of the first Xaa and
            the second Xaa and glycine residues of the second Xaa and
            and the third Xaa is replaced by an -NH-CO group.

(xi) SEQUENCE DESCRIPTION: SEQ ID NO: 32:

Pro Gln Asp Val Lys Phe Pro Xaa Xaa Xaa Gln Ile Val Gly Gly Val
           5                    10                 15

(2) INFORMATION FOR SEQ ID NO: 33:

(i) SEQUENCE CHARACTERISTICS:
        (A) LENGTH: 16
        (B) TYPE: amino acids
        (D) TOPOLOGY: linear (ii) MOLECULE TYPE: protein (ix) FEATURE:
        (D) OTHER INFORMATION: The first Xaa, the second Xaa, the
            third Xaa, and the fourth Xaa are each glycine residues
            wherein the -CO-NH- group between glycine residues of the
            first Xaa and the second Xaa and glycine residues of the
            third Xaa and the fourth Xaa is replaced by an NH-CO
            group.

(xi) SEQUENCE DESCRIPTION: SEQ ID NO: 33:

Pro Gln Asp Val Lys Phe Pro Gly Xaa Xaa Gln Ile Val Xaa Xaa Val
           5                    10                 15

What is claimed is:

1. An immunological binding compound which binds to an antibody, said antibody also binding to an epitope consisting of a naturally occurring amino acid sequence wherein said compound comprises a modified, hepatitis C virus amino acid sequence selected from the group consisting of SEQ ID NO: 30, SEQ ID NO: 31, SEQ ID NO: 32, and SEQ ID NO: 33.

2. An immunological binding compound of claim 1 wherein the amino acid sequence is SEQ ID NO: 30.

3. An immunological binding compound of claim 1, wherein the amino acid sequence is SEQ ID NO: 31.

4. An immunological binding compound of claim 1, wherein the amino acid sequence is SEQ ID NO: 32.

5. An immunological binding comprising of claim 1, wherein the amino acid sequence is SEQ ID NO: 33.

6. Composition of matter comprising the immunologic binding compound of claim 1, bound to a solid phase.

7. Method for determining an antibody in a sample, comprising contacting said sample to the immunologic binding compound of claim 1 to a solid phase, adding to said sample a labelled binding partner to form complexes of solid phase bound immunologic binding compound, antibody, and labelled binding partner, and determining bound or unbound labelled binding partner as a determination of antibody in said sample.

8. Method for determining an antibody in a sample, comprising contacting said sample to the composition of matter of claim 6, adding a labelled binding partner to said sample to form complexes of solid phase bound immunological binding compound antibody, and labelled binding partner, and determining bound or unbound labelled binding partner, and determining bound in unbound labelled binding partner as a determination of antibody in said sample.

9. The method of claim 7, wherein said labelled binding partner is labelled, immunologic binding compound.

10. The method of claim 8, wherein said labelled binding partner is labelled, immunologic binding compound.

11. The method of claim 7, wherein said labelled binding partner is an anti antibody.

12. The method of claim 8, wherein said labelled binding partner is an anti antibody.

13. The method of claim 7, wherein said labelled binding partner is labeled with an enzyme, a chemiluminescent label, or a fluorescent label.

14. The method of claim 8, wherein said labelled binding partner is labelled with an enzyme, a chemiluminescent label, or a fluorescent label.

* * * * *